United States Patent [19]

Stedronsky

[11] Patent Number: 6,034,220
[45] Date of Patent: Mar. 7, 2000

[54] CHEMICAL MODIFICATION OF REPETITIVE POLYMERS TO ENHANCE WATER SOLUBILITY

[75] Inventor: Erwin R. Stedronsky, San Diego, Calif.

[73] Assignee: Protein Polymer Technologies, San Diego, Calif.

[21] Appl. No.: 09/028,086

[22] Filed: Feb. 23, 1998

Related U.S. Application Data

[62] Division of application No. 08/343,264, Nov. 21, 1994, Pat. No. 5,760,004.

[51] Int. Cl.⁷ .......................... A61K 38/17; C07K 14/195
[52] U.S. Cl. .......................... 530/353; 530/350; 530/402; 530/408; 530/409; 530/410; 514/21; 8/127.5; 8/128.1
[58] Field of Search .................... 8/127.5, 128.1; 530/353, 402, 410

[56] References Cited

U.S. PATENT DOCUMENTS 4,224,219  9/1980  Van Blanton et al. .
5,207,941  5/1993  Kroner et al. .
5,243,038  9/1993  Ferrari et al. .

OTHER PUBLICATIONS

Tanaka et al. "Salt–Catalyzed Addition Reaction of Monoepoxides with Silk Fibroins" J. Polymer Chem. Ed., vol. 12, 2741–2754, 1974.

Morrison & Boyd, *Organic Chemistry,* Third Edition pp. 564–565, 1973.

Sakamoto et al., *Chemical Abstracts* 99:123944 (1983).

*Primary Examiner*—Michael P. Woodward
*Assistant Examiner*—Abdel A. Mohamed
*Attorney, Agent, or Firm*—Richard F. Trecartin; Flehr Hohbach Test Albritton & Herbert LLP

[57] ABSTRACT

Highly repetitive proteins which are relatively insoluble in water are chemically modified to increase solubility. The protein is reacted with a functionalizing agent to introduce additional polar functionalities and disrupt the order of the protein. The solubility of the protein in water is increased by the chemical modification, while adhesive and surfactant properties are retained.

10 Claims, No Drawings

```
SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1:

Arg Gly Asp Ser
1

(2) INFORMATION FOR SEQ ID NO:2:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Ile Lys Val Ala Val
1               5

(2) INFORMATION FOR SEQ ID NO:3:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Gly Ala Gly Ala Gly Ser
1               5
```

CHEMICAL MODIFICATION OF REPETITIVE POLYMERS TO ENHANCE WATER SOLUBILITY

This is a division of application Ser. No. 08/343,264 filed Nov. 21, 1994, now U.S. Pat. No. 5,760,004.

INTRODUCTION

1. Technical Field

The field of this invention is chemically modified, water-soluble protein polymers.

2. Background

Protein polymers have been synthesized with repeating domains of varying block size and mass ratios. Depending upon the nature of the repeating domain, the polymers of this sort may form a highly ordered structure of pleated beta-sheets. In general, as the total number of such blocks in a polymer is increased, the solubility of the polymer in water decreases. Also, the regularity of these synthesized repetitive unit proteins is much greater than the naturally occurring repetitive unit proteins from which the synthesized protein polymers are designed. In the most extreme cases, proteins composed of almost 100% silk-like blocks are totally insoluble in water.

The vast majority of plastics have hydrophobic surfaces. For many applications such as cell culture and immunodiagnostics, it is critical to have a hydrophilic surface that aqueous fluids will wet. Current treatments commercially employed include plasma treatment to cause the formation of ionizable chemical groups on the surface, oxidation under conditions of irradiation, or by deposition of surfactants on the surface.

For many such applications, it is desirable to utilize the surfactant and adhesive properties of such highly ordered protein polymers by depositing these proteins onto hydrophobic surfaces from aqueous solutions. However, due to the insolubility in water, such protein polymers must be solubilized using strongly hydrogen bonding solvents such as >85% formic acid or using concentrated aqueous solutions of salts high in the Hoffmeister series, such as 4.5 M lithium perchlorate or lithium bromide.

Such solvents have deficiencies for every day use. While >85% formic acid is a good solvent and is fully volatile, it is corrosive and the vapors are noxious. When using the aqueous salt solutions, the salt residues are corrosive and noxious. While one can devise a coating process which begins by preparing a relatively concentrated stock solution of protein polymer in a solvent such as those described above, and then diluting to the proper working concentrations using water as the diluent, this approach does not solve the problems indicated above. In addition, often, these diluted working solutions are metastable, and change their deposition characteristics with time.

The noxious and corrosive components of the existing solvent systems complicates the design of coating processes involving protein polymers with highly ordered structures. It is therefore of considerable value to provide methods of modifying such protein polymers to improve their solubility in water.

Relevant Literature

Methods for producing recombinant repeating-block proteins are described in U.S. Pat. No. 5,243,038, issued on Sep. 7, 1993; and International Application PCT US89 05016.

SUMMARY OF THE INVENTION

Methods and compositions are provided for the preparation and use of water soluble repetitive unit proteins by chemical modification of water insoluble repetitive unit proteins composed of repeating blocks of amino acid sequence. The solubility of the protein in water is increased by reaction of a polar small molecular weight reactant with available functionalities on the protein. The resulting product is water soluble, can be coated onto plastic and strongly adheres, and retains active functional sequences, particularly biological functional sequences, present in the parent compound.

DESCRIPTION OF SPECIFIC EMBODIMENTS

Methods and compositions are provided, whereby proteins having low water solubility are chemically modified by adding low molecular weight organic groups to available functionalities to produce products which are water soluble, but strongly adhere to a plastic surface, even in the presence of an aqueous medium over long periods of time. Of particular interest are high molecular weight proteins where extended stretches of small repeating units comprise a major portion of the protein.

The proteins are typically of relatively high molecular weight, being greater than about 6 kD, usually greater than about 10 kD, preferably more than 20 kD and generally less than about 250 kD, usually less than about 150 kD, more usually less than about 125 kD. The protein will be repetitive, that is, comprised of repeating units, where the individual units will have from 3–30 amino acids (9–90 nt), more usually 3 to 25 amino acids (9–75 nt), particularly 4 to 15 amino acids (12–45 nt), more particularly 4 to 12 amino acids (12–36 nt), usually having the same amino acid appearing at least twice in the same unit, generally separated by at least one amino acid. For the most part, the naturally occurring repeating units will be from about 4 to 8 amino acid repeating units, particularly, 4 to 6 amino acid units. Different amino acid repetitive unit combinations may be joined together to form a block copolymer or alternating block copolymer.

The protein will have a significant proportion of the total amino acids with a reactive functionality, which includes hydroxyl, sulfhydryl, carboxyl, and amino, particularly hydroxyl or sulfhydryl group, e.g. serine, threonine, tyrosine, cysteine, lysine, arginine, histidine, aspartic acid and glutamic acid. Usually at least about 2% by number of amino acids, more usually at least about 5% by number, and preferably at least about 10% by number, and usually not more than about 30%, more usually not more than about 20% will have the reactive functionalities involved in functionalization of the protein. Desirably, the reactive group is hydroxyl, where the hydroxyl group involved in the functionalization may vary with the functionalizing group, e.g. tyrosine reacting with an oxirane and serine reacting with a sultone.

Suitable proteins for modification will have a highly ordered, usually semi-crystalline structure, with a high degree of extended β and β-turn conformations. The protein solubility in deionized water will usually be less than about 1.0 mg/ml, more usually less than about 0.1 mg/ml, at ambient conditions. After the subject chemical modification the solubility will be at least about 10 mg/ml, more usually at least about 100 mg/ml at ambient conditions.

The protein will be modified by reaction with a functionalizing reagent, e.g. an alkylating agent, or an acylating agent, where a single reagent or a combination of reagents may be employed, usually not more than about 3 reagents, more usually not more than about 2 reagents. Suitable reagents will be of from about 2 to 8, frequently 2 to 6 carbon atoms, usually 2 to 4 carbon atoms for other than ammonio, and usually 5 to 8 for ammonio, having from 1 to 4 heteroatoms, which will be chalcogen (oxygen and sulfur), and nitrogen, particularly as amino having from 1 to 4 substituents. Functionalities will include epoxides of from 2 to 4, usually 2 to 3 carbon atoms, acyl groups of from 2 to 8, usually 2 to 6 carbon atoms, where the acyl group may have from 0 to 2 oxy groups of from 0 to 2 carbon atoms, or amino group of from 0 to 4 carbon atoms, particuary ammonio, lactones of from 3 to 5 carbon atoms, particularly sulfonate lactones (sultone) of from about 3 to 8 carbon atoms, and substituted active olefin or active halogen, of from about 2 to 8 carbon atoms, usually 2 to 6 carbon atoms and preferably 2 to 3 carbon atoms for other than ammonio substituted, usually having from 1 to 3 heteroatoms, as described above. The resulting substituents are illustrated by hydroxyethyl, hydroxypropyl, dihydroxypropyl, dihydroxybutyl, carboxymethyl, carboxyethyl, cyanoethyl, trimethylammonioethyl, 2-hydroxy-4-dimethylammoniobutyl, sulfonatopropyl, trimethylammonioacetyl, methoxyacetyl, and the like. Particular reactants include ethylene oxide, propylene oxide, hydroxypropylene oxide, epichlorohydrin, chloroacetic acid, trimethylammonioethylchloride, trimethylammoniopropylene oxide, acrylonitrile, methacrylamide, dimethylaminoethylchloride hydrochloride, etc. The reaction will usually proceed by a nucleophilic substitution at the carbon of the reagent, with retention of the amino acid heteroatom, particularly base catalysed nucleophilic substitution.

As a first step the protein willl be solubilized in a suitable solution in which the reaction can occur, usually using concentrated aqueous solutions of salts, which are both high in the Hoffmeister series and whose anions are substantially inert to the functionalizing reagent(s), usually at least about 2 M concentration, more usually at least about 4.5 M. Examples of suitable Hoffmeister salts are lithium perchlorate and potassium sulfate. For base catalyzed reactions, the pH of the solution may then be raised to at least about 9, more usually to least about 11, or at least about 10 mM, depending on the nature of the organic reactant. The functionalizing reagent will usually be added in at least 2 fold molar excess, usually at least about 10 fold excess, based on available reactive groups in the protein composition for the particular reaction. The reaction will proceed until at least about 1% of the reactive amino acid residues have been modified, more usually at least about 10% of the reactive residues have been modified, and usually not more than about 80%, more usually not more than about 60% of the reactive residues have been modified. At room temperature the reaction will usually be complete in about 6 hours, more usually about 3 hours. The reaction is stopped by lowering the pH to about 7.0 to 7.5. The modified protein may be purified by conventional methods.

Depending on the selected conditions, some degradation of the protein may occur. By using strongly basic conditions for extended periods of time, e.g. >2M, for extended periods of time, e.g. >1 h, particularly at high ionic strength, e.g. >2M $LiClO_4$, the molecular weight of the protein may be reduced by about half. Therefore, by selecting the reaction conditions, one can provide for a product which has a lower or about the same molecular weight of protein, plus the additional weight of the reactant.

Proteins of interest include structural proteins such as elastin-, collagen-, keratin-, and silk-like proteins, preferably, synthetic protein polymers, particularly proteins designed with silk-like protein repetitive units, where blocks of repetitive units, generally blocks of 2 to 50 repetitive units, are separated by sequences of from about 3 to 50, more usually 3 to 35 amino acids including a sequence which has chemical or physiological activity, e.g. cell receptor binding, such as in basement membrane proteins, ligands for receptors, homing proteins, etc. These proteins include the RGDS (SEQ ID NO: 01) sequence (fibronectin), the IKVAV (SEQ ID NO: 02) sequence (laminin), cysteine, lysine, aspartic acid, histidine, etc., and other groups, as described in U.S. patent application Ser. Nos. 609,716 and 114,618, and PCT/US87/02822 and PCT/US89/05016, where numerous repetitive unit proteins are described, as well as different intervening sequences, which references are incorporated herein by reference. The polypeptides may be natural, chemically synthesized, or recombinant proteins, including modified forms such as mutants and fusion products.

Silk-like proteins have as a repeating unit GAGAGS (SEQ ID NO: 03) (G=glycine; A=alanine; S=serine). This repeating unit is found in a naturally occurring silk fibroin protein. The N-terminus and C-terminus may be different sequences, generally of from about 1 to 125 amino acids, usually of from about 1 to 60 amino acids, usually fewer than 20%, more usually fewer than about 10% of the total amino acids of the protein. For the most part, there will be no particuar pattern of amino acids in the terminal sequences. Of particular interest are proteins which mimic the composition and physical properties of silk of *Bombyx mori*. Generally, different terminii will be the result of insertion of the gene into a vector in a manner that results in expression of a fusion protein. Any protein which does not interfere with the desired properties of the product may provide the one or both terminii. Particularly, endogenous host proteins, e.g. bacterial proteins, may be employed. The terminii are not critical to the subject invention, are primarily for convenience, but should not interfere with the desired properties of the protein, and may be designed for proteolytic cleavage.

Of particular interest is a motif having a base sequence of about 2 to 10, preferably 8 to 9, individual repeating units, usually separated by a sequence of about 5 to 160 amino acids, usually 8 to 50 amino acids, which may include an internal repeat different from the individual repeating unit of from 3 to 30 amino acids, which will normally result in modification of the physical properties and the structure of the protein. For example, by introducing elastin repeats in a fibroin-like-polymer, one can provide for greater elasticity and flexibility, in comparison to the fibroin-like-polymer. Thus, one may have block copolymers, where the properties can vary between the nature of the homopolymers of the individual repeat units. The total number of base repeating units will generally be in the range of about 50 to 300, usually 75 to 250.

Physical measurements of purified silk-like proteins, prepared by recombinant techniques and described subsequently, confirm the model of anti-parallel chain pleated sheet conformation for the crystalline regions of *Bombyx mori* silk fibroin. Circular dichroic (CD) and Fourier transform infrared (FTIR) spectroscopic analysis are consistent with a high degree of extended B and B-turn conformations. Comparisons of the spectra obtained from a silk-like protein (SlpIII described in the patent references indicated above) with that of naturally occurring silk fibroin in various solvents indicate that SlpIII in solution consists of a mixture of the random and highly ordered structures seen in silk fibroins.

A silk-like protein comprising intervening RGDS (SEQ ID NO: 01) sequences (referred to as SLPF or FCB-SLP protein in the patent references indicated above, and sold as ProNectin®-F, Protein Polymer Technologies, Inc., San Diego, Calif.) is characterized by having strong adhesive properties. On coating a plastic or glass surface, e.g. polystyrene, Bioglas, polyacrylates, etc., particularly thermal molding and extrusion plastics, a strong adherent coating is obtained, which is stable over extended periods, e.g. 30 days and more, in cellular culture. After modification, the adhesive properties as identified above are not substantially altered.

The protein compounds can be provided as aqueous solutions, where the salt content does not exceed 1 M, usually less than about 0.5 M, and may be deionized water. Usually the protein compound will be present in the aqueous solution at at least about 0.001 weight %, and may be 0.01 weight % or more, usually not more than about 90 weight %, and may be provided as solutions for direct use for coating or other purpose, as concentrates of at least about 10 weight %, or as compositions with other components appropriate for its intended purpose. The particular concentration of the protein in the solution will depend on the nature of the protein, its solubility, the intended application, other components in the solution, and the like. For example, the coating of biiologicaly functional proteins onto plastic substrates can be conducted at extremely low concentrations, whereas solutions for the spinning of fibers will be highly concentrated.

The modified proteins are particularly useful for coating plastic surfaces. The increased water solubility allows coating procedures to take place in non-toxic solvent systems where various convenient methods of application may be employed without concerns about the hazards of the previously used solvents. As numerous applications involve contact with viable biological cells or tissue, biocompatible plastics are especially preferred. Biocompatible plastics are typically non-toxic, biochemically inert. Exemplary biocompatible plastics include polycaprolactone, polycarbonate, polydimethylsiloxane (silicone rubber), polydioxanone, polyether urethane, polyethylene and polyethylene terphthalate, polyglycolic acid and polylactic acid and PLGA copolymers, polystyrene, polyhydroxyethyl methacrylate (HEMA), polymethylmethacrylate (acrylic), polyvinyl chloride (PVC), etc.

The plastic substrate may take many forms, where the plastic substrate may be labware, e.g. Petri dishes, culture bottles, Erlenmeyer flasks, slides, roller bottles, multiwell plates, or other labware where an adherent coating is desirable, for example, in which cells may be grown; devices where an adherent protein coating is desired, such as devices introduced in vivo, where the bare plastic surface of the device may cause an adverse physiological response; and fibers or films, where one wishes to modify the surface characteristics of the material; and the like. The solution may be applied to the surface by painting, spraying, dipping, or soaking.

Additives may be included in the solutions, such as stabilizers, buffers, detergents, spreading agents, or the like, generally being present in total in less than about 5 weight % of the solutin, generally less than about 1 weight % of the solution.

The following examples are offered by way of illustration and not by way of limitation.

EXPERIMENTAL

The names of the polymers and their preparation may be found in U.S. Pat. No. 5,243,038 and application Ser. No. 07/609,716, filed Nov. 6, 1990.

Hydroxypropylated SLPF

SLPF (ProNectin®-F, Protein Polymer Technologies, Inc., San Diego, Calif.) (100 mg) was dissolved in 5.0 ml of 4.5 M lithium perchlorate in water. Solid NaOH (19 mg) was dissolved in the mixture with stirring at room temperature. Propylene oxide (600 µl) was added in two portions of 300 µl each, stirring at room temperature for 2 hours after each addition. The reaction mixture was poured into 45 ml of water and was neutralized to pH 7.0–7.5 using dilute aqueous hydrochloric acid. The mixture was dialyzed for 24 hours against deionized water using a 13 kDa cutoff cellulose membrane (Spectrum Medical Devices). A slight precipitate (4.8 mg) was removed by filtration through a tared filter paper. The remaining very slight cloudiness was removed by filtration through a pad of Celite 545 to yield a clear solution of pH 6.5. This solution was concentrated on the rotary evaporator to approximately 10 ml before being again dialyzed against deionized water for 24 hours using a 13 kDa cutoff cellulose membrane. The contents of the dialysis bag were shell frozen in a 100 ml pear shaped flask and lyophilized to a final pressure of 75 mTorr at 25° C. A white fluffy fibrous solid (42.8 mg) was recovered. This material was designated HP-PnF, and was observed to be readily soluble in deionized water.

The gel electrophoresis of this material shows a set of bands which migrate at about half the molecular weight of the starting material, indicating approximately one hydrolytic chain scission per molecule occurred during the reaction chemistry. The reactivity of the silk fibroin antibody to HP-PnF was observed to be less intense than with native SLPF as judged from the intensity of the development bands on the gel and the known mass of protein sample applied to the gel.

Hydroxypropylated SLP3.0

Crude SLP3.0 (100 mg) was slurried in 4.5 ml of 4.5M lithium perchlorate and stirred for 24 hours at room temperature to yield a brown particulate suspension in a viscous solution. Celite 454 (50 mg) was added, stirred, and centrifuged to compact a brown pellet (ca. 0.3 ml volume) and provide a clear supernatant solution. The supernatant was decanted. To the supernatant, was added NaOH (20 mg) dissolved in 0.50 ml of 4.5 molar lithium perchlorate solution. Propylene oxide (300 µl) was added in one portion and the mixture stirred for 6 hours at 35° C. A second portion of propylene oxide (300 µl) was added and the mixture stirred for 2 hours. Water (5.0 ml) was added and the reaction mixture was neutralized to pH 7.0 with dilute aqueous hydrochloric acid. The solution was dialyzed through a 13 kDa cutoff cellulose membrane for 48 hours against deionized water. Slight cloudiness in the product solution was removed by centrifugation to yield a clear supernatant and a pellet (ca. 0.2 ml). The supernatant was shell frozen and lyophilized to a final pressure of 75 mTorr at 25° C. to yield a white fluffy material (39 mg). This material was designated HP-SLP3.0; and was observed to be readily soluble in deionized water.

The gel electrophoresis of this material shows a set of bands which migrate at about half the molecular weight of the starting material, indicating approximately one hydrolytic chain scission per molecule. The reactivity of the silk fibroin antibody to HP-SLP3.0 was observed to be less intense than with native SLP3.0 as judged from the intensity of the development bands on the gel and the known mass of protein sample applied to the gel.

Dimethylaminoethylated SLP3

Crude SLP3.0 (1.0 g) was stirred with 25 ml of 4.5M $LiClO_4$ for 16 hr. Undissolved suspended solids were removed by centrifugation using a S534 rotor at 15,000 rpm for 20 min. A light yellow clear supernatant (23.5 ml) was recovered and used subsequently. Four portions of dimethylaminoethylchloride HCl (0.72 g, 5 mMole) and sodium hydroxide (0.40 g, 10 mMole) were added, stirring 30 min. after each portion. Acetic acid (1140 μL) was added to adjust to pH 6.5. The neutralized solution was placed in a 13 kDa cutoff dialysis bag and dialyzed against deionized water for 24 hr. The retentate was filtered through a pad of Celite 545 on a Buchner funnel, concentrated on the rotary evaporator, and dialyzed through a 13 kDa cutoff dialysis bag against deionized water for 24 hours. The retentate was shell frozen and lyophilized to yield 39.5 mg of white product. This material was designated DMA-SLP3.0 and was observed to be readily soluble in deionized water.

Sulfopropylated SLP3

Crude SLP3.0 (1.0 g) was stirred with 25 ml of 4.5M LiClO$_4$ for 16 hr. Undissolved suspended solids were removed by centrifugation using a S534 rotor at 15,000 rpm for 20 min. A light yellow clear supernatant (23.5 ml) was recovered and used subsequently. Four portions of propane sultone (1.22 g; 876 μL; 10 mMole) and sodium hydroxide (0.40 g, 10 mMole) were added, stirring 30 min. after each portion. Acetic acid (600 μL) was added to adjust to pH 6.5. The neutralized solution was placed in a 13 kDa cutoff dialysis bag and dialyzed against deionized water for 24 hr. The retentate was filtered through a pad of Celite 545 on a Buchner funnel, concentrated on the rotary evaporator, and dialyzed through a 13 kDa cutoff dialysis bag against deionized water for 24 hours. The retentate was shell frozen and lyophilized to yield 160 mg of white product. This material was designated SP-SLP3.0 and was observed to be readily soluble in deionized water.

Sulfopropylated SLPF

SLPF (103 mg) and 3.0 ml of 4.5 molar aqueous lithium perchlorate was added to a 10 ml Erlenmeyer flask fitted with a rubber septum cap and agitated by a magnetic stirrer. The head space was purged with nitrogen and stirring commenced at ambient temperature. Propane sultone, dissolved in 2.0 ml of tetrahydrofuran, was added in one portion to yield a homogeneous mixture. A solution (1.0 ml) of sodium hydroxide (40 mg) dissolved in 4.5 molar aqueous lithium perchlorate was then added by syringe pump at a rate of 0.019 ml/min. After stirring for an additional 30 minutes a solution of acetic acid (60 mg) in water (1.0 ml) was added in one portion and the reaction mixture was transferred to a 13 kDa cutoff dialysis bag and dialyzed against 15 L of deionized water for 24 hr. The water was replaced and dialysis was continued for an additional 24 hours. The retentate was shell frozen and lyophilized to yield 90 mg of white product. This material was designated SP-SLPF and was observed to be readily soluble in deionized water.

Dimethylaminoethylated SLPF

SLPF (103 mg), dimethylaminoethylchloride hydrochloride (360 mg), and 3.0 ml of 4.5 molar aqueous lithium perchlorate were added to a 10 ml Erlenmeyer flask fitted with a rubber septum cap and agitated by a magnetic stirrer. The head space was purged with nitrogen and stirring commenced at ambient temperature. A solution of sodium hydroxide (200 mg) dissolved in 4.5 molar aqueous lithium perchlorate (2.65 ml) was then added by syringe pump at a rate of 0.174 ml/min. After stirring for an additional 60 minutes, acetic acid was used to adjust to pH 6.0–6.5, and the reaction mixture was transferred to a 13 kDa cutoff dialysis bag and dialyzed against 15 L of deionized water for 24 hr. The retentate was shell frozen and lyophilized to yield 63 mg of white product. This material was designated DMA-SLPF and was observed to be readily soluble in deionized water.

Amino Acid Compositions

The amino acid composition of the derivatized protein polymers were determined by the PTC derivatization procedure of Henrickson and Meredith (1984). Protein samples were hydrolysed with 5.7 N constant boiling hydrochloric acid at 108° C. for 24 hours in vacuo. After reaction with PITC, amino acid derivatives were detected at 254 nm by HPLC reverse phase chromatography using a Hewlett Packard 1090 system and a Supelco C18 column (4.6 mm×25 cm) with a linear gradient of 0–50% acetonitrile in 0.1 molar ammonium acetate pH 6.78 as a mobile phase. Henrickson, R. L. and Meredith, S. C. (1984) Amino Analysis by Reverse Phase High Performance Liquid Chromatography. *Anal. Biochem.* 137:65–74. The normalized results of these analyses are presented in Tables 1 through 5 for HP-PnF, HP-SLP3.0, DMA-SLP3.0, SP-SLP3.0, and SP-PnF respectively.

TABLE 1

Normalized Amino Acid Compositions of HP-PnF.

| Component | picoMole (found) | Ratios (theoret) | Ratios (found) | Deficit |
|---|---|---|---|---|
| L-Glycine | 6623 | 30 | 30 | 0 |
| L-Alanine | 4707 | 23 | 21.3 | −7% |
| L-Serine | 2091 | 11 | 9.5 | −14% |
| L-Tyrosine | 57 | 1 | 0.3 | −70% |
| L-Threonine | 201 | 1 | 0.9 | −10% |

TABLE 2

Normalized Amino Acid Compositions of HP-SLP3.0.

| Component | picoMole (found) | Ratios (theoret) | Ratios (found) | Deficit |
|---|---|---|---|---|
| L-Glycine | 6774 | 29 | 29 | 0 |
| L-Alanine | 4520 | 20 | 19.4 | −3% |
| L-Serine | 1831 | 9 | 7.8 | −14% |
| L-Tyrosine | 60 | 1 | 0.3 | −70% |

TABLE 3

Normalized Amino Acid Compositions of DMA-SLP3.0.

| Component | picoMole (found) | Ratios (theoret) | Ratios (found) | Deficit |
|---|---|---|---|---|
| L-Glycine | 2487 | 29 | 29 | 0 |
| L-Alanine | 1621 | 20 | 18.9 | −5% |
| L-Serine | 602 | 9 | 7.0 | −22% |
| L-Tyrosine | 74 | 1 | 0.9 | −10% |

TABLE 4

Normalized Amino Acid Compositions of SP-SLP3.0.

| Component | picoMole (found) | Ratios (theoret) | Ratios (found) | Deficit |
|---|---|---|---|---|
| L-Glycine | 4856 | 29 | 29 | 0 |
| L-Alanine | 3135 | 20 | 18.7 | −6% |
| L-Serine | 632 | 9 | 3.8 | −58% |
| L-Tyrosine | 67 | 1 | 0.4 | −60% |

TABLE 5

Normalized Amino Acid Compositions of SP-PnF.

| Component | picoMole (found) | Ratios (theoret) | Ratios (found) | Deficit |
|---|---|---|---|---|
| L-Glycine | 4269 | 30 | 30 | 0 |
| L-Alanine | 2972 | 23 | 20.9 | −9% |
| L-Serine | 1426 | 11 | 10.0 | −9% |
| L-Tyrosine | 133 | 1 | 0.9 | −10% |
| L-Threonine | 143 | 1 | 1.0 | 0 |

In the cases of SP-SLP3.0 and of SP-PnF, the deficits of amino acids can be verified by means of microchemical analysis of the elemental compositions of the proteins and calculation of the molar ratio of sulfur to nitrogen. Both the SLP3.0 and SLPF molecules are initially devoid of sulfur, and each functionalization event introduces a single 3-sulfopropyl moiety. Thus the molar ratio of sulfur to nitrogen is a measure of the extent of the functionalization reaction.

From the observed deficits of amino acids in SP-SLP3.0, the predicted ratio of S/N=0.120. From microanalysis of elemental composition of this functionalized protein, the measured ratio of S/N=0.119. From the observed deficits of amino acids in SP-PnF, the predicted ratio of S/N=0.042. From microanalysis of elemental composition of the functionalized protein, the measured ratio of S/N=0.034. Thus data on elemental compositions and on amino acid compositions are consistent with each other.

The data in Table 1 through 5 focus on the amino acids which make up the silk fibroin region (GAGAGS (SEQ ID NO: 03)) of these protein polymers containing silk-like regions. In all cases, the normalized ratios indicate a depletion of L-serine. Such results implicate the L-serine residues as the primary sites of the various etherification reactions, through reaction on the side chain hydroxyls.

An O-alkylated residue of L-serine in the modified protein polymer is expected to hydrolyze back to an amino acid, but not to cleave back to native L-serine under the conditions of the acid hydrolysis step of the amino acid compositional analysis. Thus, the absolute content of L-serine observed in the modified protein polymers will appear to be reduced, as is observed. On a basis of this compositional data, functionalization occurs on from 9% to 58% of the L-serine residues.

The reactivity of the antibody to silk fibroin depends upon recognition of the GAGAGS (SEQ ID NO: 03) epitope. If a chemical modification occurs at the most prominent chemical group within this epitope, the hydroxyl side chain on the L-serine residue, then a reduced reactivity with the antibody would be anticipated. Qualitatively, such reduced reactivity with the antibody is observed in the cases of HP-PnF and HP-SLP3.0.

Attachment of VERO Cells On Polystyrene Coated With HP-PnF

In order to judge the competence of HP-PnF with respect to surfactant activity and cell attachment activity, a cell attachment assay was performed on a multi-well polystyrene tissue culture plate with 96 wells. In this assay, ProNectin F (PnF) was made up in 4.5 molar lithium perchlorate at 1.0 mg/ml and was serially diluted with phosphate buffered saline to the final coating concentrations. The HP-PnF was made up in deionized water, and serially diluted with deionized water. Each dilution was applied to one lane of 8 wells on the plate. Blocking, inoculation with cells, incubation, fixation, and staining with amido blue black dye were all conducted according to standard protocols. Relative cell numbers were estimated spectrophotometrically at 495 nm. The results of this cell attachment assay are reported in Table 6.

TABLE 6

VERO Cell Attachment On Serially Diluted ProNectin ®F And On Serially Diluted HP-PnF

| Coating Solution (μg/ml) | Dose per Well (g/well) | Absorbance PnF | Absorbance HP-PnF |
|---|---|---|---|
| 20 | $2.0 \times 10^{-6}$ | 0.775 ± 0.024 | 0.758 ± 0.031 |
| 4.0 | $4.0 \times 10^{-7}$ | 0.761 ± 0.016 | 0.799 ± 0.038 |
| 0.80 | $8.0 \times 10^{-8}$ | 0.781 ± 0.021 | 0.795 ± 0.019 |
| 0.16 | $1.6 \times 10^{-8}$ | 0.764 ± 0.026 | 0.776 ± 0.015 |
| 0.032 | $3.2 \times 10^{-9}$ | 0.771 ± 0.033 | 0.768 ± 0.024 |
| 0.0063 | $6.3 \times 10^{-10}$ | 0.737 ± 0.040 | 0.558 ± 0.075 |
| 0 | 0 | 0 | 0 |

Attachment of VERO Cells on Polystyrene Coated With SP-PnF

In order to judge the competence of SP-PnF with respect to surfactant activity and cell attachment activity, a cell attachment assay was performed on a multi-well polystyrene tissue culture plate with 96 wells. In this assay, ProNectin F was made up in 4.5 molar lithium perchlorate at 1.0 mg/ml and serially diluted with phosphate buffered saline to the final coating concentration of 10 μg/ml, and then applied to the first lane of 8 wells. The SP-PnF was dissolved in deionized water at 1 mg/ml and diluted to the final coating concentrations of 10 μg/ml, 1.0 μg/ml, and 0.10 μg/ml. Each dilution was applied to two lanes of 8 wells on the plate. Blocking, inoculation with cells, incubation, fixation, and staining with amido blue black dye were all conducted according to standard protocols. Relative cell numbers were estimated spectrophotometrically at 495 nm.

The results of this assay are reported in Table 7.

TABLE 7

VERO Cell Attachment On ProNectin ®F And On Serially Diluted SP-PnF

| Coating Solution (μg/ml) | Dose per Well (g/well) | Absorbance PnF |
|---|---|---|
| Negative Control | 0.0 | 0.047 ± 0.004 |
| ProNectin F at 10 μg/ml | $1.0 \times 10^{-5}$ | 0.683 ± 0.017 |
| SP-PnF at 10 μg/ml | $1.0 \times 10^{-5}$ | 0.724 ± 0.015 |
| SP-PnF at 1.0 μg/ml | $1.0 \times 10^{-6}$ | 0.741 ± 0.023 |
| SP-PnF at 0.1 μg/ml | $1.0 \times 10^{-7}$ | 0.731 ± 0.032 |

Attachment of VERO Cells On Polystyrene Coated With DMA-PnF

In order to judge the competence of DMA-PnF with respect to surfactant activity and cell attachment activity, a cell attachment assay was performed on a multi-well polystyrene tissue culture plate with 96 wells. In this assay, ProNectin F was made up in 4.5 molar lithium perchlorate at 1.0 mg/ml and serially diluted with phosphate buffered saline to the final coating concentration of 10 μg/ml, and then applied to the first lane of 8 wells. The DMA-PnF was dissolved in deionized water at 1 mg/ml and diluted to the final coating concentrations of 10 μg/ml, 1.0 μg/ml, and 0.10 μg/ml. Each dilution was applied to one lane of 8 wells on the plate. Blocking, inoculation with cells, incubation, fixation, and staining with amido blue black dye were all conducted according to standard protocols. Relative cell numbers were estimated spectrophotometrically at 495 nm.

The results of this assay are reported in Table 8.

TABLE 8

VERO Cell Attachment On ProNectin ®F And On Serially Diluted DMA-PnF

| Coating Solution ($\mu$g/ml) | Dose per Well (g/well) | Absorbance PnF |
|---|---|---|
| Negative Control | 0.0 | 0.044 ± 0.002 |
| ProNectin F at 10 $\mu$g/ml | $1.0 \times 10^{-5}$ | 0.728 ± 0.042 |
| SP-PnF at 10 $\mu$g/ml | $1.0 \times 10^{-5}$ | 0.771 ± 0.022 |
| SP-PnF at 1.0 $\mu$g/ml | $1.0 \times 10^{-6}$ | 0.715 ± 0.029 |
| SP-PnF at 0.1 $\mu$g/ml | $1.0 \times 10^{-7}$ | 0.652 ± 0.031 |

The data show that HP-PnF retains its activity as both a surfactant and as a cell attachment surface modifier. Furthermore, the hydroxypropylation does not cause any acute cytotoxicity. The hydroxypropylated polymer shows utility for coating polystyrene for purposes of mammalian cell culture. The modification also makes it suitable for other purposes, such as deposition on polypropylene fibers.

It is evident from the data presented that the subject methods increase the water solubility of highly repetitive, ordered proteins, without decreasing the protein's adhesive properties. After modification, the proteins can be solubilized in water, and used to coat plastic surfaces for biological purposes, eliminating the need for solubilizing in toxic solutions.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of preparing a water soluble protein from a water insoluble, at least partially crystalline, repetitive unit precursor protein comprising a naturally occurring amino acid having a reactive heteroatom containing functionality, said method comprising:

dissolving said precursor protein in an organic solvent, high salt concentration aqueous solvent, or combination thereof, to provide a reaction solution;

adding to said reaction solution an organic reactant under conditions for reaction of said organic reactant with said functionality to retain said heteroatom and provide at least one polar additional heteroatom, whereby at least 1% of said amino acids are functionalized;

whereby said water soluble protein is produced.

2. A method according to claim 1, wherein said repetitive unit is a fibroin repetitive unit.

3. A method according to claim 1, wherein said solvent is an aqueous high ionic strength solution.

4. A method according to claim 3, wherein said solution is at least 2 M in a lithium salt and said condition is a pH of at least 9.

5. A method according to claim 4, wherein said organic reactant is an epoxide of from 2 to 5 carbon atoms.

6. A method of preparing a water soluble protein from a water insoluble, at least partially crystalline, fibroin repetitive unit precursor protein comprising serine or threonine as a member of said repetitive unit, said method comprising:

dissolving said precursor protein in a high salt concentration basic aqueous solvent to provide a reaction solution;

adding to said reaction solution an epoxide of from 2 to 5 carbon atoms, whereby at least 1% of said amino acids are functionalized to provide said water soluble protein.

7. A method according to claim 6, wherein said aqueous solvent is at least 2 M in a lithium salt and has an hydroxide concentration of at least about 10 mM.

8. A method according to claim 6, wherein said precursor protein comprises intervening groups comprising a cell binding sequence.

9. A method of preparing a water soluble protein from a water insoluble, at least partially crystalline, repetitive unit precursor protein comprising serine or threonine in said repetitive unit, said method comprising:

dissolving said precursor protein in a basic high salt concentration aqueous solvent, to provide a reaction solution;

adding to said reaction solution an organic reactant under conditions for reaction of said organic reactant with said functionality to retain said heteroatom and provide at least one polar additional heteroatom functionality selected from the group consisting of hydroxyl, sulfonate, and ammonio, whereby at least 1% of said amino acids are functionalized;

whereby said water soluble protein is produced.

10. A method according to claim 9, wherein said additional heteroatom functionality is hydroxyl and said reactant is an expoxide of from 2 to 4 carbon atoms.

* * * * *